United States Patent [19]

Jokura et al.

[11] Patent Number: 5,641,495
[45] Date of Patent: Jun. 24, 1997

[54] SKIN COSMETIC CONTAINING CERAMIDES OF PSEUDOCERAMIDES AND DICARBOXYLIC ACIDS AND DICARBOXYLIC ACID SALTS

[75] Inventors: Yoji Jokura; Toshio Uesaka; Seiji Honma; Yuri Kato; Koichi Ishida, all of Tokyo, Japan

[73] Assignee: Kao Corporation, Tokyo, Japan

[21] Appl. No.: 544,279

[22] Filed: Oct. 17, 1995

[30] Foreign Application Priority Data

Oct. 19, 1994 [JP] Japan .................. 6-253187

[51] Int. Cl.$^6$ .................. A61K 7/40; A61K 7/48
[52] U.S. Cl. .................. 424/401; 514/784; 514/847; 554/66
[58] Field of Search .................. 424/401; 514/844, 514/847, 784; 554/66

[56] References Cited

U.S. PATENT DOCUMENTS

| | | | |
|---|---|---|---|
| 4,089,942 | 5/1978 | Bore et al. | 424/47 |
| 4,268,424 | 5/1981 | Hall et al. | 252/546 |
| 4,950,688 | 8/1990 | Bowser et al. | 514/560 |
| 5,141,964 | 8/1992 | Noel | 514/777 |
| 5,198,210 | 3/1993 | Critchley et al. | 424/78.03 |
| 5,221,757 | 6/1993 | Ohashi et al. | 554/66 |
| 5,424,324 | 6/1995 | Willingham | 514/372 |
| 5,451,691 | 9/1995 | Crawford et al. | 554/68 |

FOREIGN PATENT DOCUMENTS

| | | |
|---|---|---|
| 851922 | 6/1977 | Belgium . |
| 05085924 | 4/1993 | Japan . |
| 06065053 | 3/1994 | Japan . |

Primary Examiner—Melvyn I. Marquis
Assistant Examiner—Robert H. Harrison
Attorney, Agent, or Firm—Oblon, Spivak, McClelland, Maier & Neustadt, P.C.

[57] ABSTRACT

A skin cosmetic causing little irritation and having an excellent moisturizing effect which contains the following components (A), (B) and (C):

(A) a ceramide or a pseudoceramide represented by the following formula (1) or (2):

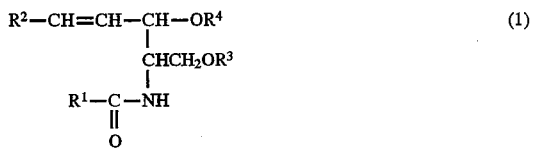

(1)

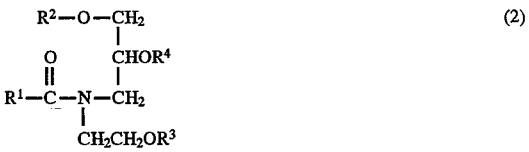

(2)

wherein $R^1$ and $R^2$ represent each a $C_9$ to $C_{39}$ hydrocarbon group; and $R^3$ and $R^4$ represent each H, a phosphate residue, a sulfate residue, etc.;

(B) a dicarboxylic acid; and (C) a salt of a dicarboxylic acid.

8 Claims, No Drawings

SKIN COSMETIC CONTAINING CERAMIDES OF PSEUDOCERAMIDES AND DICARBOXYLIC ACIDS AND DICARBOXYLIC ACID SALTS

FIELD OF THE INVENTION

This invention relates to a skin cosmetic. More particularly, it relates to a skin cosmetic which has an excellent moisturizing effect, little irritates the skin and is suitable for the application to the face skin.

BACKGROUND OF THE INVENTION

It has been known that the moisture in the keratinous layer plays an important role of moistening and softening the skin and that water soluble components of the keratinous layer (i.e., free amino acids, urea, organic acids, inorganic ions, etc.) participate in the retention of the moisture. Accordingly, these water soluble substances are used in dermatologic preparations and cosmetics in order to ameliorate or prevent skin chapping.

For the same purposes, there have been developed and employed various moisturizing substances having strong affinities for water. When applied to the skin, however, such a moisturizing substance remains on the keratinous layer of the skin and supplies moisture thereto. Moreover, it can exert only a temporary effect. Thus it can neither fundamentally improve the moisture retention of the keratinous layer nor essentially prevent or treat skin chapping.

On the other hand, it is known that ceramides, which are contained in the keratinous layer of the skin, contribute to the barrier function and moisture retention of the skin. It is also known that the external use of ceramides is efficacious in treating dry skin. Therefore, attempts have been made to synthesize ceramides or analogues of the same (i.e., pseudoceramides). For example, methods for producing ceramides per se are described in JP-A-59-7118 (the term "JP-A" as used herein means an "unexamined published Japanese patent application") and WO 93/22281, while methods for producing pseudoceramides are described in, for example, JP-A-62-228048, JP-A-63-22107, JP-A-63-216812, JP-A-63-218609, JP-A-63-227513, JP-A-63-227514, JP-A-63-228048, JP-A-63-297309, JP-A-64-9906, JP-A-64-9907, JP-A-64-29347, JP-A-64-31752, JP-A-64-79195, JP-A-4-225907, JP-A-4-282304, JP-A-4-342553, EP No. 554303 and EP No. 555250.

Recently, it has been also proposed to use ceramides and/or pseudoceramides together with hydroxycarboxylic acids such as glycolic acid or lactic acid to thereby efficaciously ameliorate dry skin (EP No. 587288 corresponding to JP-A-6-157283). However, it is known that hydroxycarboxylic acids would irritate the skin when applied to a sensitive part such as the face. It is therefore difficult to use a hydrocarboxylic acid in such an amount as to give a satisfactory effect as a component of a face cosmetic.

SUMMARY OF THE INVENTION

Thus, an object of the present invention is to provide a skin cosmetic having an excellent moisturizing effect and causing no irritation even though it is applied to the face.

Under these circumstances, the present inventors have conducted extensive studies. As a result, they have successfully found out that a skin cosmetic, which has an excellent moisturizing effect, little irritates the skin and can be suitably applied to the face, can be obtained by using a combination of a ceramide or a pseudoceramide with a dicarboxylic acid and a dicarboxylic acid salt, thus completing the present invention.

DETAILED DESCRIPTION OF THE INVENTION

Accordingly, the present invention provides a skin cosmetic characterized by comprising the following components (A), (B) and (C):

(A) a ceramide or a pseudoceramide represented by the following formula (1) or (2):

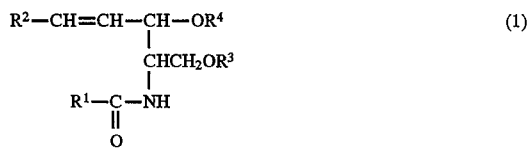

wherein $R^1$ and $R^2$ are either the same or different and each represents a linear or branched, saturated or unsaturated hydrocarbon group having from 9 to 39 carbon atoms which is unsubstituted or substituted with one or more hydroxyl groups; and $R^3$ and $R^4$ are either the same or different and each represents a hydrogen atom, a phosphate residue, a sulfate residue or a sugar residue;

(B) a dicarboxylic acid represented by the following formula (3):

wherein X represents a divalent hydrocarbon group having from 1 to 6 carbon atoms; and (C) a salt of a dicarboxylic acid represented by the above formula (3).

The ceramide or pseudoceramide to be used as the component (A) in the present invention is one represented by the above formula (1) or (2). Examples of the linear or branched, saturated or unsaturated hydrocarbon group having from 9 to 39 carbon atoms, which is represented by $R^1$ or $R^2$ in the formula, include alkyl groups (for example, nonyl, decyl, undceyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, 2-heptylundecyl, 5,7,7-trimethyl-2-(1,3,3-trimethylbutyl)-octyl, 2-hexyldecyl, 2-octylundecyl, 2-decyltetradecyl); decocyl, dodecenyl, undecenyl, tridecenyl, tetradecenyl, pentadecenyl, hexadecenyl, heptadecenyl, octadecenyl, nonadecenyl, eicosenyl, heneicosenyl, docosenyl, tricosenyl, tetracosenyl, pentacosenyl, hexacosenyl, nonadienyl, decadienyl, dodecadienyl, undecadienyl, tridecadienyl, tetradecadienyl, pentadecadienyl, hexadecadienyl, heptadecadienyl, octadecadienyl, nonadecadienyl, icosadienyl, henicosadienyl, docosadienyl, tricosadienyl, tetracosadienyl, pentacosadienyl, hexacosadienyl, 9-octadecenyl and 9,12-octadecadienyl groups. These hydrocarbon groups may be substituted with one or more hydroxyl groups.

It is preferable that $R^1$ and $R^2$ are alkyl groups having from 9 to 28 carbon atoms, which may be substituted with hydroxyl group(s), selected from among the above-mentioned ones.

The ceramides represented by the formula (1) to be used as the component (A) may be those extracted and purified from brain or skin. Alternatively, chemically synthesized ones may be used therefor. They can be chemically synthesized in accordance with, for example, the methods described in JP-A-59-7118 and WO 93/22281.

Particularly preferable examples of the ceramides (1) include N-oleoylshingosine, N-(12-hydroxyoctadecanoyl) sphingosine, N-(16-hydroxyhexadecanoyl)sphingosine and bovine brain ceramide.

On the other hand, the pseudoceramides represented by the formula (2) can be produced in accordance with, for example, the methods described in JP-A-62-228048 and JP-A-63-216852. As particularly preferable examples of the pseudoceramide (2), compounds represented by the following formula (4) may be cited.

wherein $R^5$ represents an alkyl group having from 9 to 17 carbon atoms; and $R^6$ represents an alkyl group having from 10 to 18 carbon atoms.

To achieve a satisfactory moisturizing effect, it is preferable that the content of the component (A) in the skin cosmetic of the present invention ranges from 0.01 to 20% by weight, still preferably from 0.05 to 15% by weight and still preferably from 0.1 to 10% by weight.

The dicarboxylic acid to be used as the component (B) in the present invention is one represented by the above formula (3). Particular examples thereof include malonic acid (X=CH$_3$), succinic acid (X=CH$_2$CH$_2$), fumaric acid, maleic acid (X=CHCH), glutaric acid (X=CH$_2$CH$_2$CH$_2$), adipic acid (X=CH$_2$CH$_2$CH$_2$CH$_2$), phthalic acid and terephthalic acid (X=Ph).

The dicarboxylic acid salt to be used as the component (C) in the present invention is not particularly restricted, so long as it is a salt of the dicarboxylic acid represented by the above formula (3). Examples of the dicarboxylic acid salt include alkali metal (for example, sodium, potassium) salts; alkali earth metal (for example, calcium, magnesium) salts; alkanolamine (for example, triethanolamine) salts; basic amino acid (for example, lysine, arginine) salts and ammonium salts. These dicarboxylic acid salt may be added in the form of a salt at the step of the preparation of the skin cosmetic of the present invention. Alternatively, an acid may be added followed by the addition of an alkali (sodium hydroxide, etc.) to thereby form the aimed salt via neutralization in the system.

To achieve a sufficient moisturizing effect while avoiding excessive irritation, it is preferable that the total content of these components (B) and (C), in terms of the acid, in the skin cosmetic of the present invention falls within a range of from 0.01 to 20% by weight, still preferably from 0.05 to 15% by weight and still preferably 0.01 to 10% by weight.

To achieve a sufficient moisturizing effect while avoiding irritation due to the acid, it is preferable that the molar ratio of the components (B) to (C) falls within a range of from 1/9 to 9/1, still preferably from 2/8 to 8/2.

Moreover, it is preferable to regulate the pH value of the skin cosmetic of the present invention, which contains the components (B) and (C), to pH 3 to 10, still preferably to pH 3 to 9. Thus a sufficient moisturizing effect can be achieved while avoiding the irritation observed at a pH value less than 3 or exceeding 10.

The skin cosmetic of the present invention may further contain other components commonly employed in cosmetics (oily substances, water, surfactants, etc.) and processed into a desired preparation (an emulsion, a dispersion, a two-layer preparation, a solubilizing agent, a gel, etc.) to thereby give a lotion, a milky lotion, a cream, a pack, a foundation, etc.

Examples of the oily substances include hydrocarbons (for example, solid or liquid paraffin, crystal oil, ceresin, ozokerite, montan wax, squalane, squalene), olive oil, carnauba wax, lanolin, jojoba oil, ester oils (for example, glycerol monostearate, glycerol distearate, glycerol monooleate, isopropyl stearate, neopentyl glycol dicaprate, cholesterol isostearate), higher fatty acids (for example, stearic acid, palmitic acid), higher alcohols (for example, cetanol, stearyl alcohol) and sterols (for example, cholesterol).

When these oily substances are employed, the content of the same in the skin cosmetic preferably ranges from 0.01 to 50% by weight, still preferably from 0.1 to 30% by weight.

Water is usable as a base together with ethanol or water-soluble polyhydric alcohols. It is particularly preferable to use water-soluble polyhydric alcohols since the moisturizing effect can be further improved thereby. Examples of the water-soluble polyhydric alcohols are those having two or more hydroxyl groups per molecule such as ethylene glycol, propylene glycol, 1,3-butylene glycol, 1,4-butylene glycol, dipropylene glycol, glycerol, polyglycerol (for example, diglycerol, triglycerol, tetraglycerol), glucose, maltose, maltitol, sucrose, fructose, xylitol, sorbitol, maltotriose, threitol, erythritol and those obtained by reducing starch decomposition sugars. Either one of these water-soluble polyhydric alcohols or a mixture thereof may be used in the present invention.

When water, ethanol and/or these water-soluble polyhydric alcohols are employed, the content of the same in the skin cosmetic may be appropriately determined depending on the preparation form. It is usually preferable that the total content thereof ranges from 0.01 to 95% by weight, still preferably from 0.1 to 90% by weight.

When the skin cosmetic of the present invention is to be processed into an emulsion, a solubilizing agent, etc., it is preferable to add surfactants thereto. Examples of the surfactants include polyoxyethylene alkyl ethers, polyoxyethylene fatty acid esters, polyoxyethylene sorbitan fatty acid esters, polyoxyethylene sorbitol fatty acid esters, glycerol fatty acid esters, polyoxyethylene hardened castor oil alkyl sulfates, polyoxyethylene alkyl sulfates, alkyl phosphates, polyoxyethylene alkyl phosphates, alkali metal salts of fatty acids, sorbitan fatty acid esters, glycerol fatty acid esters an alkyl glyceryl ethers. Either one of these surfactants or a mixture thereof may be used in the present invention.

When these surfactants are employed, the content thereof in the skin cosmetic preferably ranges from 0.01 to 50% by weight, still preferably from 0.1 to 30% by weight.

The skin cosmetic of the present invention may further contain silicones as an oil or a surfactant. The silicones are not particularly restricted but may be arbitrarily selected from among those commonly employed in cosmetics. Examples thereof include octamethylpolysiloxane, tetradecamethylpolysiloxane, methylpolysiloxane, methylpolysiloxane high polymer, methylphenylpolysiloxane, methylpolycyclosiloxane (for example, octamethylcyclotetrasiloxane, decamethylcyclopentasiloxane), trimethylsiloxysilicic acid and modified silicones (for example, polyether-modified silicone, polyether/alkyl-modified silicone, alkyl glyceryl ether-modified silicone).

When these silicones are employed as an oil or a surfactant, the content of the same in the skin cosmetic may be controlled so as to regulate the total content respectively with non-silicone oil(s) or non-silicone surfactant(s) to the level as defined above.

Furthermore, a powder may be added to the skin cosmetic of the present invention to thereby give a makeup cosmetic such as a foundation. Examples of the powder include loading pigments (for example, mica, talc, sericite, kaolin, nylon powder, polymethylsilsesquioxane), inorganic pigments (for example, pearl), organic pigments (for example, Red no. 202, Red No. 226, Yellow No. 4, aluminum lake) and inorganic powders for UV protection (for example, zinc oxide, titanium oxide, zirconium oxide, iron oxide). As these powders, use can be made of those treated with silicones (by using, for example, methyl hydrogen methylpolysiloxane, trimethylsiloxysilicic acid, methylpolysiloxane), fluorine (by using, for example, perfluoroalkyl phosphates, perfluoroalcohols), amino acids (by using, for example, N-acylglutamic acid), lecithin, metal soaps, fatty acids or alkyl phosphates.

When these powders are employed, the content of the same in the skin cosmetic may be appropriately regulated depending on the preparation form. In usual, the content preferably ranges from 0.1 to 50% by weight, still preferably from 1 to 30% by weight.

The skin cosmetic of the present invention may further contain various components which are commonly used in cosmetics, quasi drugs, medicines, etc., so long as the objects of the present invention are not deteriorated thereby. Examples of these components include inorganic salts (for example, magnesium sulfate, potassium sulfate, sodium sulfate, magnesium chloride, sodium chloride); viscosity regulating agents (for example, polyvinyl alcohol, carboxy vinyl polymer, carboxymethyl cellulose, gelatin, tragacanth gum, xanthan gum, hyaluronic acid, tuberose extract, agarose, sodium alginate); preservatives (for example, paraben); UV absorbers; colorants; medicinal components such as whitening agents, vitamins, steroidal anti-inflammatory agents, nonsteroidal anti-inflammatory agents, antihistamines, antibiotics, bactericides and fungicides; and perfumes.

Because of being less irritative and having an excellent moisturizing effect, the skin cosmetic of the present invention is not only usable in treating dry skin in winter but also applicable to the skin around eyes to thereby prevent crow's feet.

To further illustrate the present invention in greater detail, and not by way of limitation, the following Examples will be given.

EXAMPLE 1

Emulsion cosmetics having the compositions as specified in Tables 1 and 2 were prepared in a conventional manner and used to thereby evaluate the moisture contents in the keratinous layer and skin chapping scores. Table 3 shows the results.

EVALUATION METHOD

Emulsion cosmetics differing from each other were applied respectively to the right and left cheeks of 10 female subjects, who were aged 20 to 40 and suffered from chapping in cheeks in winter, once a day for 3 weeks. On the next day of the completion of the test period (3 weeks), the following items were examined.

(1) Moisture content in keratinous layer

After washing the face with water at 37° C., each subject rested quietly for 30 minutes in a room controlled at a temperature of 20° C. and a humidity of 40%. Then the moisture content in the keratinous layer was measured with an impedance meter (manufactured by IBS) and referred to as an index of the moisturizing effect of the corresponding cosmetic. Namely, a larger moisture content meant the higher moisturizing effect. The data are expressed in average ± standard deviation.

(2) Skin chapping score

The chapped skin was observed with the naked eye and evaluated in accordance with the following criteria. Each score is expressed in average ± standard deviation.

| Score: | evaluation of skin chapping |
|---|---|
| 0 | not chapped. |
| 1 | slightly chapped. |
| 2 | chapped. |
| 3 | somewhat seriously chapped. |
| 4 | seriously chapped. |

TABLE 1

| | Invention product | | |
|---|---|---|---|
| Component (% by weight) | 1 | 2 | 3 |
| methyl branched isostearyl glyceryl ether | 2.0 | — | — |
| arginine monocetylphosphate | — | 2.0 | — |
| polyoxyethylene (20) sorbitan monostearate | — | — | 1.0 |
| sorbitan monostearate | — | — | 1.0 |
| 2-octyldodecyl myristate | 10.0 | 10.0 | 10.0 |
| vaseline | 3.0 | 3.0 | 3.0 |
| squalane | 5.0 | 5.0 | 5.0 |
| tocopherol acetate | 0.5 | 0.5 | 0.5 |
| compound 1 | 2.0 | 2.0 | 2.0 |
| succinic acid | 1.0 | 1.0 | 1.0 |
| potassium succinate trihydrate | 1.0 | 1.0 | 1.0 |
| water | balance | — | — | compound 1: N-oleoylshingosine [in the formula (1) $R^1$ = cis-$CH_8H_{17}CH=CH(CH_2)_7$, $R^2 = C_{13}H_{27}$, $R^3 = R^4 = H$].

TABLE 2

| | Invention product | | | Comparative product | |
|---|---|---|---|---|---|
| Component (% by weight) | 4 | 5 | 6 | 1 | 2 |
| methyl branched isostearyl glyceryl ether | 2.0 | 2.0 | 2.0 | 2.6 | 2.0 |
| 2-octyldodecyl myristate | 10.0 | 10.0 | 10.0 | 10.0 | 10.0 |
| vaseline | 3.0 | 3.0 | 3.0 | 3.0 | 3.0 |
| squalane | 5.0 | 5.0 | 5.0 | 5.0 | 5.0 |
| tocopherol acetate | 0.5 | 0.5 | 0.5 | 0.5 | 0.5 |
| glycerol | 1.0 | 1.0 | 1.0 | 1.0 | 1.0 |
| compound 2 | 3.0 | — | — | 3.0 | — |
| compound 3 | — | 3.0 | — | — | — |
| compound 4 | — | — | 3.0 | — | — |
| succinic acid | 2.4 | 2.4 | 2.4 | — | 2.4 |
| sodium succinate | 1.0 | 1.0 | 1.0 | — | 1.0 |
| water | balance | ← | ← | ← | ← |
| pH of aqueous phase | 4.1 | 4.1 | 4.1 | 4.1 | 4.1 | compound 2: N-(12-hydroxyoctadecanoyl)sphingosine [in the formula (1), $R^1 = C_6H_{13}CH(OH)(CH_2)_{10}$, $R^2 = C_{13}H_{27}$, $R^3 = R^4 = H$].
compound 3: N-(16-hydroxyhexadecanoyl)sphingosine [in the formula (1), $R^1 = HO(CH_2)_{15}$, $R^2 = C_{13}H_{27}$, $R^3 = R^4 = H$].
compound 4: N-(3-hexadecyloxy-2-hydroxypropyl)-N-2-hydroxyethyl hexadecanamide [in the formula (1), $R^1 = C_{15}H_{31}$, $R^2 = C_{16}H_{33}$, $R^3 = R^4 = H$].

TABLE 3

| | Moisture content in keratinous layer | Skin chapping score |
|---|---|---|
| invention product 1 | 30 ± 2.8 | 0.9 ± 0.2 |
| invention product 2 | 32 ± 4.0 | 1.0 ± 0.3 |
| invention product 3 | 33 ± 3.3 | 0.9 ± 0.2 |
| invention product 4 | 25 ± 3.1 | 1.1 ± 0.3 |
| invention product 5 | 28 ± 4.2 | 0.8 ± 0.2 |

TABLE 3-continued

| | Moisture content in keratinous layer | Skin chapping score |
|---|---|---|
| invention product 6 | 32 ± 2.9 | 0.9 ± 0.2 |
| comparative product 1 | 10.5 ± 2.0 | 3.5 ± 0.8 |
| comparative product 2 | 11.2 ± 4.0 | 2.3 ± 0.4 |

EXAMPLE 2

O/W Type Moisturizing Milky Lotion

An O/w type milky lotion of the composition as will be shown hereinbelow was prepared in a conventional manner.

The milky lotion thus obtained was excellent in moisturizing effect, caused no irritation and contributed to the smoothening of the skin.

| (Component) | (% by weight) |
|---|---|
| compound 4 (the same as the one of Example 1) | 3.0 |
| cetyl alcohol | 1.0 |
| beeswax | 0.5 |
| vaseline | 2.0 |
| squalane | 6.0 |
| dimethylpolysiloxane (6 cSt) | 2.0 |
| glycerol | 4.0 |
| 1,3-butylene glycol | 4.0 |
| polyoxyethylene (10) monoleate | 1.0 |
| glycerol monostearate | 1.0 |
| tuberose polysaccharide (1% solution) | 10.0 |
| succinic acid | 0.5 |
| sodium succinate | 0.5 |
| water | the balance |
| | 100.0 |

EXAMPLE 3

Sunscreen Milky Lotion With Moisturizing Effect

A sunscreen milky lotion of the composition as will be shown hereinbelow was prepared in a conventional manner.

The milky lotion thus obtained was excellent in moisturizing effect, caused no irritation and contributed to the smoothening of the skin.

| (Component) | (% by weight) |
|---|---|
| compound 4 (the same as the one of Example 1) | 2.0 |
| octyl p-methoxycinnamate | 6.0 |
| 4-tert-butyl-4-methoxybenzoylmethane | 2.0 |
| oleyl oleate | 5.0 |
| dimethylpolysiloxane (6 cSt) | 3.0 |
| vaseline | 0.5 |
| cetyl alcohol | 1.0 |
| sorbitan sesquioleate | 0.8 |
| polyoxyethylene (20) oleyl alcohol ether | 1.2 |
| dipropylene glycol | 6.0 |
| ethanol | 3.0 |
| hydroxyethylcellulose | 0.3 |
| fumaric acid | 0.4 |
| sodium fumarate | 0.5 |

| (Component) | (% by weight) |
|---|---|
| water | the balance |
| | 100.0 |

While the invention has been described in detail and with reference to specific embodiments thereof, it will be apparent to one skilled in the art that various changes and modifications can be made therein without departing from the spirit and scope thereof.

What is claimed is:

1. A skin cosmetic characterized by comprising the following components (A), (B) and (C):
   (A) a ceramide or a pseudoceramide represented by the following formula (1) or (2):

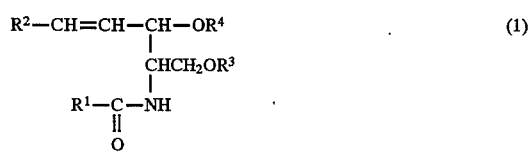

(1)

(2)

wherein $R^1$ and $R^2$ are either the same or different and each represents a linear or branched, saturated or unsaturated hydrocarbon group having from 9 to 39 carbon atoms which is unsubstituted or substituted with one or more hydroxyl groups; and $R^3$ and $R^4$ are either the same or different and each represents a hydrogen atom, a phosphate residue, a sulfate residue or a sugar residue;
   (B) a dicarboxylic acid represented by the following formula (3):

$$HOOC\text{---}X\text{---}COOH \quad (3)$$

wherein X represents a divalent hydrocarbon group having from 1 to 6 carbon atoms; and
   (C) a salt of a dicarboxylic acid represented by the above formula (3).

2. A skin cosmetic as claimed in claim 1 which contains a ceramide or a pseudoceramide of the component (A) in an amount of from 0.01 to 20% by weight.

3. A skin cosmetic as claimed in claim 1 which contains a dicarboxylic acid and a dicarboxylic acid salt in a total amount of from 0.01 to 20% by weight.

4. A skin cosmetic as claimed in claim 1 wherein the molar ratio of a dicarboxylic acid to a dicarboxylic acid salt falls within a range of from 1/9 to 9/1.

5. A skin cosmetic as claimed in claim 2 wherein the molar ratio of a dicarboxylic acid to a dicarboxylic acid salt falls within a range of from 1/9 to 9/1.

6. A skin cosmetic as claimed in claim 3 wherein the molar ratio of a dicarboxylic acid to a dicarboxylic acid salt falls within a range of from 1/9 to 9/1.

7. A skin cosmetic as claimed in any of claims 1 to 4, 5 and 6, wherein said dicarboxylic acid is one selected from among malonic acid, succinic acid, fumaric acid, maleic acid, glutaric acid, adipic acid, isophthalic acid, phthalic acid and terephthalic acid.

8. A skin cosmetic as claimed in any of claims 1 to 4, 5 and 6 which contains a dicarboxylic acid and a dicarboxylic acid salt and has a pH value of from 3 to 10.

* * * * *